US00PP17261P2

(12) United States Plant Patent
Oud

(10) Patent No.: US PP17,261 P2
(45) Date of Patent: Dec. 5, 2006

(54) ***PETUNIA* PLANT NAMED 'PETPUR'**

(50) Latin Name: *Petunia hybrida*
Varietal Denomination: Petpur

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 15 days.

(21) Appl. No.: 11/224,649

(22) Filed: Sep. 12, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Anne Marie Grunberg
*Assistant Examiner*—Georgia Helmer
(74) *Attorney, Agent, or Firm*—Bruce Vrana

(57) ABSTRACT

A new and distinct cultivar of *Petunia* plant named 'Petpur' characterized by its trailing, outwardly spreading and mounded plant habit, freely branching habit, freely flowering habit, single flowers that are deep purple in color, and good garden performance.

1 Drawing Sheet

Latin name of the genus and species of the plant claimed: *Petunia hybrida.*
Varietal denomination: 'Petpur'.

BACKGROUND OF THE NEW PLANT

The present invention relates to a new and distinct cultivar of *Petunia* plant botanically known as *Petunia hybrida* and referred to by the cultivar name 'Petpur.'

The new *Petunia* is the product of a planned breeding program conducted by the inventor in Enkhuizen, Netherlands. The new *Petunia* cultivar is freely flowering with trailing and spreading plant habit and attractive leaf and flower coloration.

The new *Petunia* originated from a cross-pollination made by the inventor in August 1999 of a proprietary selection of *Petunia hybrida* identified as code number 'Y 927,' not patented, as the female, or seed parent, with a proprietary selection of *Petunia hybrida* identified as code number 'X 909,' not patented, as the male, or pollen parent. The new *Petunia* was selected as a single plant from the resulting progeny of the cross-pollination in a controlled environment in Enkhuizen, Netherlands in June 2000.

Asexual reproduction of the new cultivar by terminal vegetative cuttings since June 2000, in Enkhuizen, Netherlands has shown that the unique features of this new *Petunia* are stable and reproduced true to type in successive generations.

SUMMARY OF THE INVENTION

Plants of the cultivar 'Petpur' have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Petspebl.' These characteristics in combination distinguish 'Petspebl' as a new and distinct cultivar:

1. Trailing, outwardly spreading and mounded plant habit
2. Freely branching habit
3. Freely flowering habit
4. Single flowers that are deep purple in color
5. Good garden performance In side-by-side comparisons conducted in Enkhuizen, Netherlands, plants of the new *Petunia* differed from plants of the female parent selection in the following characteristics:

1. Plants of the new *Petunia* have a slightly mounded habit whereas the flowers of the female selection are more flat, also the flowers of the new *Petunia* are slightly bigger for the flowers of the female selection are smaller.

In side-by-side comparisons conducted in Enkhuizen, Netherlands, plants of the new *Petunia* differed from plants of the male parent selection in the following characteristics:

1. Plants of the new *Petunia* and the male parent selection differed in flower size the flowers of the new *Petunia* have smaller flowers that the plants of the male parent selection.

Plants of the new *Petunia* 'Petpur' differ from the *Petunia* cultivar Surfinia 'Shihi purple' (Shihi Brilliant), not patented, in flower shape. The flower petals of the new *Petunia* have a more rounded apex whereas the flowers-petals of the *Petunia* cultivar Surfinia 'Shihi purple' have a more pointed apex.

The new *Petunia* also differs from the *Petunia* cultivar Surfinia 'Shihi purple' foliage color. The foliage of the new *Petunia* is more dark green whereas the foliage of the cultivar Surfinia 'Shihi purple' is lighter in color.

DESCRIPTION OF THE DRAWING

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia.*

DESCRIPTION OF THE NEW CULTIVAR

The observations and measurements describe plants grown in Enkhuizen, The Netherlands., practice circumstances outdoor in windowboxes during the summer with day temperatures ranging from 18 to 25° C. and night temperatures ranging from 10 to 14° C. Plants used for the photographs and description were about 12 weeks from planting rooted cuttings.

In the following description, color references are made to The Royal Horticultural Society Colour Chart, 1995 Edition, except where general terms of ordinary dictionary significance are used.

The plant:

*Classification.*—Botanical: *Petunia hybrida.*

*Parentage.*—Female parent: Proprietary selection of *Petunia hybrida* identified as Code number 'Y 927,' not patented. Male parent: Proprietary selection of *Petunia hybrida* identified as code number 'X 909,' not patented.

Propagation:

*Type cutting.*—Terminal vegetative cuttings.

*Time to initiate roots.*—Summer and winter: About 12 days at 20° C.

*Time to develop roots, summer R.*—About 21 days at 20° C.

*Time to develop roots, winter.*—About 28 days at 16° C.

*Root description.*—Fine, fibrous, white in color.

*Rooting habit.*—Freely branching.

Plant description:

*Form.*—Annual flowering plant; indeterminate; initially upright then trailing and outwardly spreading; uniformly mounded plant form. Freely branching habit; about eight basal branches each with about four to six lateral branches. Pinching enhances development of lateral branches.

*Usage.*—Appropriate for hanging baskets, window boxes, patio containers and landscape applications.

*Plant height.*—About 18 cm.

*Plant diameter* (*area of spread*).—About 45 cm.

*Vigor.*—Vigorous; rapid growth rate.

*Lateral branches.*—Length: About 40 cm. Diameter: About 3 mm. Internode length: About 1–4 cm. Texture: Pubescent. Color: 144C.

*Foliage description.*—Arrangement: Alternate before flowering; opposite after flowers develop; simple. Length: About 5 cm. Width: About 2.8 cm. Shape: Elliptic. Apex: Acute. Base: Attenuate. Margin: Entire. Texture, upper and lower surfaces: Sparsely pubescent; glandular. Venation pattern: Reticulate.

*Color.*—Developing and fully expanded leaves, upper surface: 147A. Developing and fully expanded leaves, lower surface: 147A. Venation, lower surface: 146C. Petiole length: About 8 mm. Petiole diameter: About 3 mm. Petiole color, upper and lower surfaces: 146C. Petiole texture: Sparsely pubescent.

Flower description:

*Flower type and habit.*—Single salverform flowers; flowers face mostly upward and outward; axillary. Freely flowering habit, about two to three open flowers and about three flower buds per lateral branch at a time.

*Natural flowering season.*—Long day responsive; long flowering period, spring until frost in the autumn; flowering continuous during this period. Plants start flowering about eight weeks after planting rooted cuttings. Flowers persistent.

*Flower longevity on the plant.*—About seven to ten days.

*Fragrance.*—Faint, sweet.

*Flower size.*—Diameter: About 7 cm. Tube length: About 4 cm. Throat diameter, distal end: About 1.3 cm. Tube diameter, proximal end: About 3 mm.

*Flower buds.*—Length: About 4.8 cm. Diameter: About 7 mm. Shape: Elongated oblong with ruffled apices. Color: More grey than 79A.

*Petals.*—Quantity/arrangement: About five petals fused in a single whorl, funnelform. Length from throat: About 4.2 cm. Width: About 3.5 cm. Shape: Roughly fan-shaped. Apex: Rounded. Margin: Entire, undulate. Texture, upper and lower surfaces: Smooth velvety.

*Color.*—When opening, upper surface: Darker than N74A. When opening, lower surface: 72B, venation 176A. Fully opened, upper surface: Brighter than 74A. Fully opened, lower surface: 72A, venation 144C to 176A. Flower throat (inside): 83B. Flower tube (outside): 79C. Venation, throat: N92A. Venation, tube: 146D to 176A.

*Sepals.*—Arrangement/appearance: Single whorl of five sepals fused at base, star-shaped. Length: About 2 cm. Width: About 2 mm. Shape: Ligulate. Apex: Rounded. Margin: Entire. Texture, upper and lower surfaces: Pubescent. Color, upper surface: 147A. Color, lower surface: 147B.

*Peduncles.*—Length: About 2.2 cm. Width: About 1 mm. Angle: About 45 to 60° from the stem. Strength: Strong. Texture: Pubescent. Color: 144C.

*Reproductive organs.*—Stamens, quantity per flower: About five. Anther shape: Ovoid. Anther size: About 1.5 mm by 1 mm. Anther color: 97C. Pollen amount: Scarce. Pollen color: 97C. Pistils, quantity per flower: One. Pistil length: About 2 cm. Style length: About 1.7 cm. Style color: 144C. Stigma shape: Anvil-shaped. Stigma color: 144A. Ovary color: 145A. Seed/fruit: Seed and/or fruit production has not been observed.

Disease and pest resistance: Plants of the new *Petunia* have not been noted to be resistant to pathogens or pests common to *Petunia.*

Garden performance: Plants of the new *Petunia* have been observed to have good garden performance. Plants of the new *Petunia* have been noted to tolerate rain, wind, and temperatures from 0 to 30° C.

What is claimed is:

1. A new and distinct cultivar of *Petunia* plant named 'Petpur', as substantially illustrated and described herein.

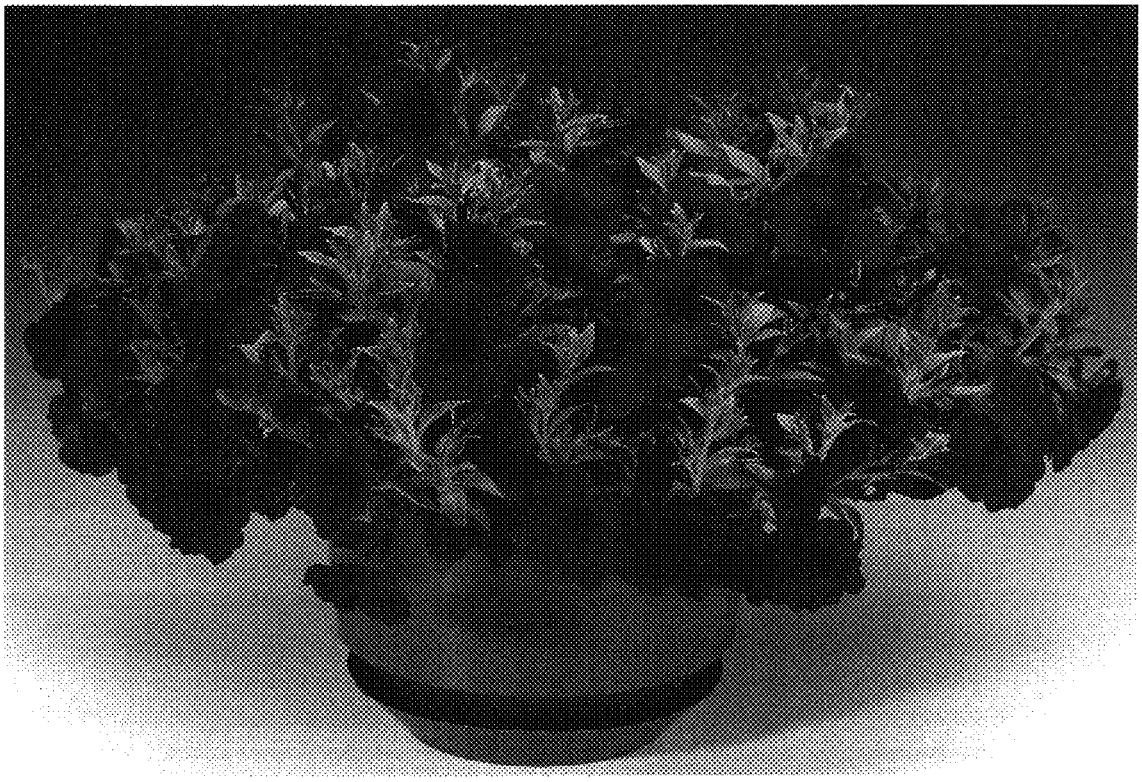

* * * * *